United States Patent [19]

Leslie

[11] 4,381,800

[45] May 3, 1983

[54] PIPE TESTER PLUG

[75] Inventor: Bruce E. Leslie, Baden, Pa.

[73] Assignee: Thaxton Inc., Gibsonia, Pa.

[21] Appl. No.: 297,578

[22] Filed: Aug. 31, 1981

[51] Int. Cl.³ ............................................. F16L 55/10
[52] U.S. Cl. ........................................ 138/90; 73/49.5
[58] Field of Search ...................... 73/49.5, 49.1, 49.8; 220/233, 235; 138/89, 94, 89.1, 90

[56] References Cited

U.S. PATENT DOCUMENTS

| | | | |
|---|---|---|---|
| 2,873,764 | 2/1959 | Lombard et al. | 73/49.5 |
| 3,886,977 | 6/1975 | Dorgebray | 138/89 |
| 4,114,654 | 9/1978 | Richardson | 138/89 |
| 4,282,982 | 8/1981 | Nuesslein | 138/89 |

*Primary Examiner*—Edward R. Kazenske
*Assistant Examiner*—David R. Schuster

[57] ABSTRACT

A high pressure pipe tester plug for insertion into a pipe having a joint such as a weld to be tested includes a stem terminating in a fixed tapered washer, a plurality of grip segments arranged about the stem, an annular floating mandrel positioned about the stem and having an upper retaining section, a cylindrical section and a tapered entry section, an O-ring positioned in an internal recess of the floating mandrel and a ring-shaped seal, rectangular in cross section, positioned about the cylindrical section of the floating mandrel and retained by the upper retaining section. When tightened by a nut, the floating mandrel is forced into the top end of the grip segments, the washer is forced into the bottom end of the grip segments and the ring-shaped seal engages the pipe interior to isolate the joint to be tested.

7 Claims, 7 Drawing Figures

PIPE TESTER PLUG

FIELD OF THE INVENTION

My invention relates to pipe stoppers and, more particularly, to high pressure pipe tester plugs which are inserted into a pipe so as to isolate a particular joint such as a weld for hydrostatic testing.

DESCRIPTION OF THE PRIOR ART

Pipe stoppers have been used heretofore in the testing of pipe, tubing, boilers, heat exchangers and other types of pressure vessels. Generally, the entire pipe length including the joint is sealed at both ends by an appropriate pipe stopper and hydrostatic pressures up to 3000 psi and greater are introduced through the pipe stopper to test the adequacy of the joint of the pipe connection.

A typical high pressure pipe tester plug includes a fixed mandrel attached to a stem which is surrounded by a plurality of steel grips. A washer engages a steel grip at the end opposite the mandrel and a nut forces the washer onto the grips which hold against the inside wall of the pipe when the nut is tightened. At the same time a seal cup attached to the fixed mandrel is compressed to make a tight seal. Since both ends of the pipe are closed, the stem includes a clearthrough passage for filling and venting.

Other forms of general pipe stoppers are found in U.S. Pat. Nos. 3,613,936; 3,494,504; 3,291,156; 3,667,640; 2,993,616; 3,370,614; 2,835,404; 1,600,137; 3,749,131; 3,618,811; 2,855,003; and 1,335,117.

SUMMARY OF THE INVENTION

My high pressure pipe tester plug eliminates the need to test whole sections of pipe containing the joint to be tested. In addition, my invention eliminates the need for welding plugs or nipples onto standard socket weld openings in order to conduct pressure tests. My pipe tester plug is easily installable and with appropriate replacement of the various seals, the useful life of the plug is substantial.

My invention is a high pressure pipe tester plug which is inserted into a pipe having a joint such as a weld to be tested. The plug is inserted into the pipe just downstream of the joint to be tested thereby isolating the joint from the balance of the pipe. The testing equipment is installed at the open end of the pipe or fitting thereby defining a small volume of pipe for testing.

The plug itself includes a stem having a threaded section, a smooth section and terminating in a fixed tapered washer. A plurality of grip segments are arranged cylindrically about the stem and have tapered openings at each end. An annular floating mandrel is positioned about the stem for cooperation with the top end of the grip segments. The floating mandrel includes an upper retaining section, an adjacent cylindrical section and a tapered entry section. An O-ring is positioned in an internal recess in the floating mandrel and is adapted for sealable engagement with the smooth section of the stem. A ring-shaped seal, rectangular in cross section, is positioned about the cylindrical section of the floating mandrel and retained by the upper retaining section thereof. A nut threadably engages the threaded portion of the stem and, when tightened, forces the floating mandrel into the top end of the grip segments causing the O-ring to sealably engage the stem and the ring-shaped seal to engage the pipe interior to isolate the joint for testing.

DESCRIPTION OF THE PREFERRED EMBODIMENTS

Figure 1:
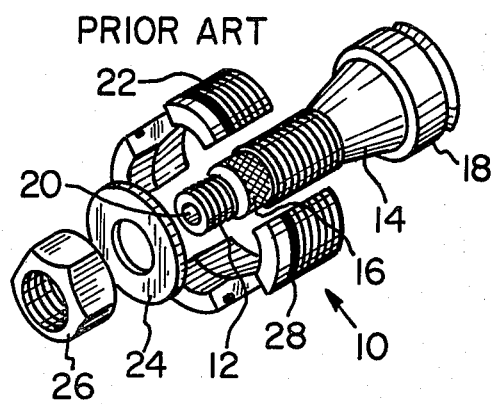
FIG. 1 is an exploded view of a prior art pipe stopper.

The prior art pipe stopper, generally designated 10, is illustrated in FIG. 1. A threaded stem 12 terminates in a conical-shaped fixed mandrel 14 having an appropriate stop at its terminal end. Adjacent the threaded section of the stem 12 is a knurled section 16 for ease of handling. A neoprene seal cup 18 is positioned about the mandrel 14 against the stop. A plurality of steel grips 22 are held in place about the threaded stem 12 by means of an appropriate O-ring 28. Depending on the size of the pipe stopper, more than one O-ring may be employed to retain the steel grips 22 in place and form appropriate seals with the pipe interior. A washer 24 is positioned over the threaded stem 12 and a nut 26 threadably engages the stem 12 so as to force the washer 24 against the steel grips 22 causing the steel grips 22 to diverge as they move along the tapered mandrel and cause the neoprene seal cup 18 to compress and expand outwardly against the pipe interior. The stem 12 includes a clearthrough opening 20 through which the pipe to be tested is filled or vented. Such pipe stoppers are used to close off the ends of the pipes as entire pipes or pressure vessels are subjected to high pressure testing.

Figure 2:
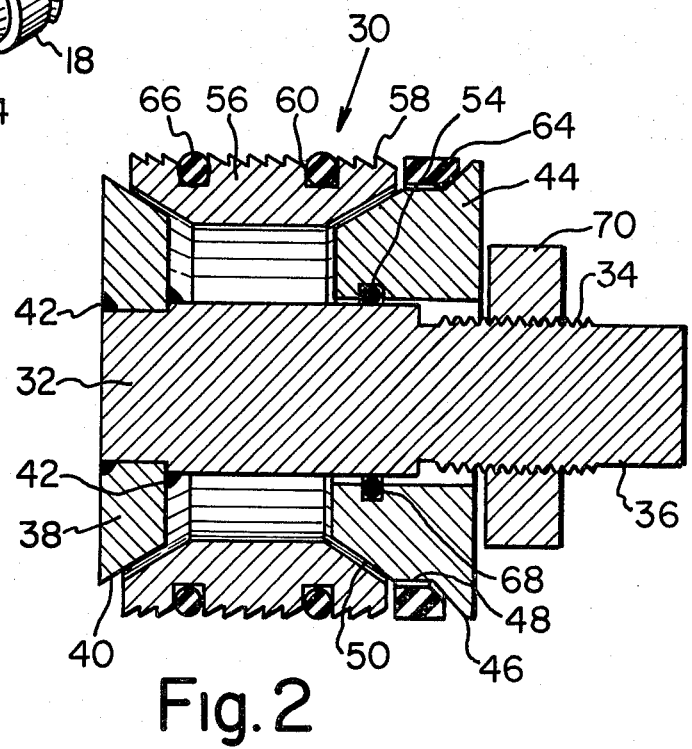
FIG. 2 is a section taken through the axial center line of my high pressure pipe plug.
Figure 3:
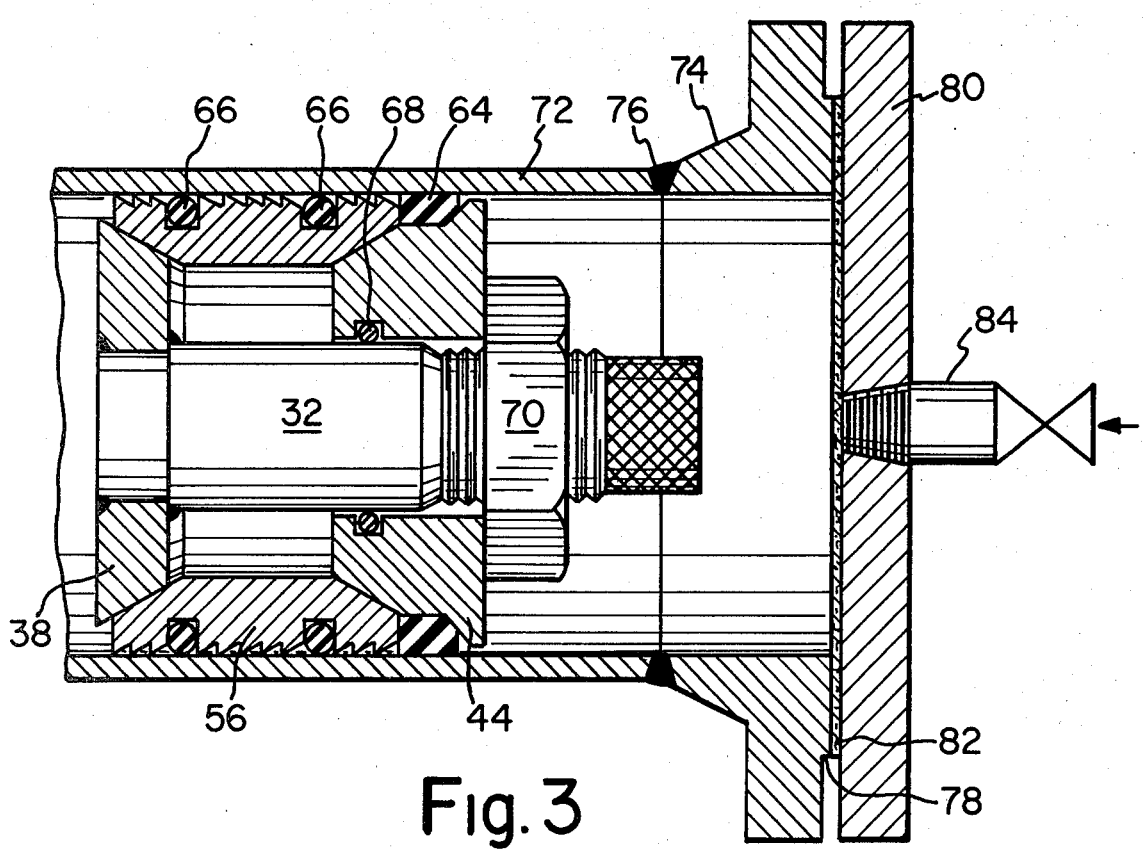
FIG. 3 is a view partly in section taken through a pipe having a weld joint to be tested and including my plug.

My pipe tester plug, generally designated 30, is intended to be used internally of a pipe 72 so as to be positioned just downstream of a connection such as weld 76 which is to be isolated for high pressure testing, FIGS. 2 and 3.

My pipe tester plug 30 includes a stem 32, a frustoconical fixed washer 38 attached at the end of the stem 32, a floating mandrel 44, a plurality of steel grips 56, external O-rings 66, an internal O-ring 68, a ring-shaped seal 64 and a nut 70 to retain the plug in assembled relationship, FIG. 2.

Figure 4:
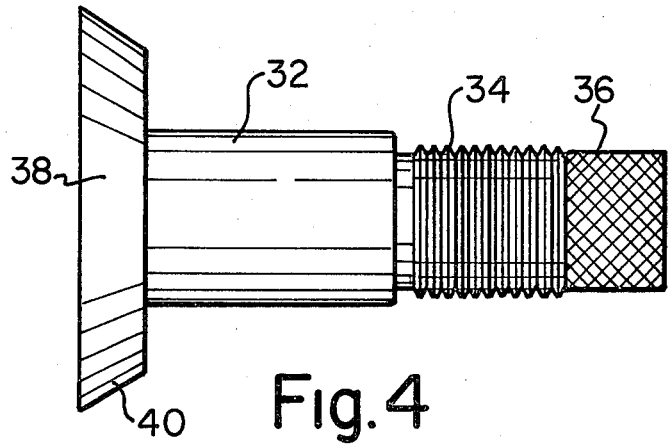
FIG. 4 is a frontal elevation of the plug stem.

The stem 32 terminates in a frustoconical-shaped washer 38 having tapered conical surface 40, FIGS. 2 and 4. The frustoconical-shaped washer 38 is fixed to the stem 32 by welds 42, FIG. 4. The stem 32 is unthreaded in the area adjacent the washer 38 and also includes a threaded section 34 and a terminal knurled section 36 for ease in handling.

Figure 5:
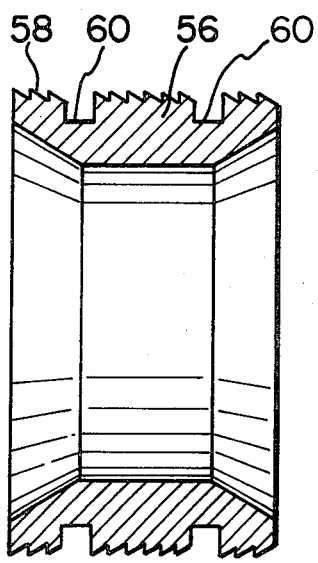
FIG. 5 is a section through the axial center line of the steel grips.

The steel grips 56 (FIGS. 2 and 5) are formed in a plurality of sections which, when assembled, form a cylinder capable of being expanded, in the same manner as the prior art grips of FIG. 1. The steel grips which have tapered entry sections at each end include external gripping threads 58 for engagement with the interior of the pipe wall. The gripping threads or grooves are each formed of two intersecting sidewalls and the sidewalls are sloped so that the sidewall nearest the upstream end of the grip has a substantially greater included angle with a radial plane than the intersecting sidewall which is nearer the downstream end of the grip. The terms upstream and downstream are used in reference to the direction of introduction of the ultimate testing fluid.

Figure 6:
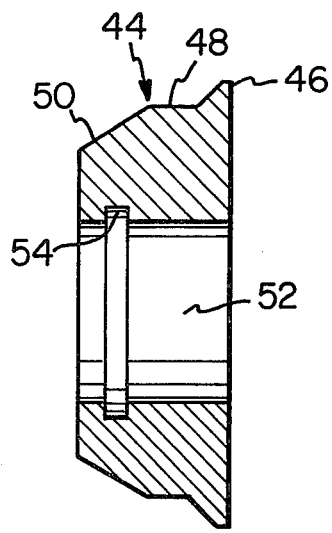
FIG. 6 is a section through the floating mandrel.

The floating mandrel 44 includes a tapered retaining lip 46 at its upstream end, an adjacent cylindrical section 48 and terminates at its downstream end in a frustoconical tapered section 50, FIG. 6. The floating mandrel 44 has an internal bore 52 extending clearthrough and communicating with the internal bore 52 is an internal recess 54 nearer the downstream end than the upstream end and in the area of the tapered section 50 for accommodating the O-ring 68, FIG. 2.

Figure 7:
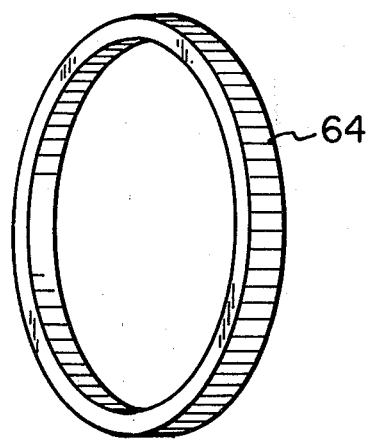
FIG. 7 is an isometric of the ring-shaped seal.

The seal 64 is ring-shaped and rectangular in cross section, FIG. 7. The seal ring 64 is normally made of neoprene or its equivalent. It is dimensioned so as to fit on the cylindrical section 48 of the floating mandrel 44 and to be retained thereon by the tapered retaining lip 46, FIG. 2.

The O-rings 66 positioned in the external recesses 60 of the steel grips 56 retain the steel grips about the stem 32. The entire plug 30 is held in assembled relationship by means of nut 70 which threadably engages with threaded section 34.

My high pressure pipe tester plug 30 is illustrated in the installed condition in FIG. 3. A pipe 72 is connected to a flange 74 by means of an appropriate weld 76. The flange 74 terminates in a raised face or lip 78. A blind flange 80 of a hydrostatic testing machine (not shown) is connected to the flange 74 and an appropriate gasket 82 positioned therebetween. This connection is normally by means of nuts and bolts (not shown) extending through the two flanges. After testing the blind flange is replaced by the appropriate valve or other flanged fitting. A threaded connection 84 permits the appropriate pressure testing equipment to be attached.

The pipe tester plug 30 is installed in the interior of the pipe just downstream of the weld 76 prior to connecting the blind flange 80 in place. The pipe tester plug 30 is installed in place by a socket wrench and appropriate extension. The nut 70 is turned causing the floating mandrel 44 to travel along the respective sloped surfaces of the steel grips with a resultant outward expansion of the steel grips as well as the seal 64 which is compressed and expanded outwardly between the top of the steel grips and the retainer lip of the floating mandrel 44. An internal seal is created between the floating mandrel 44 and the unthreaded portion of the stem 32 by means of the internal O-ring 68.

It can be seen that only a small volume of pipe must now be tested to determine the effectiveness of the weld joint 76. This is an appreciable savings over previous pipe testing techniques which require plugging opposing ends along pipe sections and/or flanges and which require testing over the entire length of such an arrangement.

The various metal components are normally made of carbon steel case hardened by carbonizing or the like and which are substantially cadmium or zinc plated.

The high pressure plugs can be made in a number of diameters with the 2 inches through 20 inches being representative. A plug for a 4⅛ inch I.D. pipe has tested successively at 3800 psi.

Various modifications can be made to the subject invention as fall within the scope of the following claims.

I claim:

1. A high pressure plug for insertion into a pipe having a joint to be tested comprising:
    A. a stem having a threaded section and a smooth section and terminating at a first end in a fixed tapered washer;
    B. a plurality of grip segments arranged in cylindrical form about the stem and having aligned tapered openings at a bottom end and a top end, said tapered bottom end adapted to cooperate with the washer;
    C. an annular floating mandrel positioned about the stem and comprised of an upper retaining section, an adjacent cylindrical section, a tapered entry section adapted for cooperation with the top end of the grip segments, a central bore and an internal annular recess communicating with the central bore;
    D. an O-ring positioned in the internal recess of the floating mandrel and adapted for sliding sealable engagement with the smooth section of the stem;
    E. a ring-shaped seal rectangular in cross section positioned about the cylindrical section of the floating mandrel and retained by the upper retaining section; and
    F. a nut for threadably engaging the threaded portion of the stem and engageably forcing the floating mandrel into the top end of said grip segments,
whereby said O-ring sealably engages said stem and said seal engages the pipe interior to isolate the joint and define a small volume for testing.

2. The plug of claim 1, said grip segments including at least one external annular recess, accommodating an O-ring for sealable engagement with the pipe interior.

3. The plug of claim 1, said grip segments being externally grooved with each groove formed of two intersecting sidewalls, said sidewall nearest the top end forming a substantially greater included angle with a radial plane than the sidewall nearest the bottom end.

4. The plug of claim 1, said tapered washer being integrally welded to said stem.

5. The plug of claim 1, said stem terminating in a knurled section at a second end.

6. The plug of claim 1, said internal annular recess positioned in the area of the tapered entry section.

7. In combination a pipe joined to a pipe flange or the like by a weld and a high pressure test plug sealably positioned within said pipe interior immediately downstream of the weld to define a small volume in the area of the weld for hydrostic testing, said test plug comprising:
    A. a stem having a threaded section and a smooth section and terminating at a first end in a fixed tapered washer;
    B. a plurality of grip segments arranged in cylindrical form about the stem and having aligned tapered openings at opposing ends with one end cooperating with the washer and at least one extended annular recess accommodating an O-ring in sealable engagement with the pipe interior;
    C. an annular floating mandrel positioned about the stem and comprised of an upper retaining section, an adjacent cylindrical section, a tapered entry section in cooperation with the other end of the grip segments, a central bore and an internal annular recess communicating with the central bore;
    D. an O-ring positioned in the internal recess of the floating mandrel in sealable engagement with the smooth section of the stem;
    E. a ring-shaped seal rectangular in cross section positioned about the cylindrical section of the floating mandrel and retained by the upper retaining section and the grip segments in sealable engagement with the pipe interior; and
    F. a nut threadably engaging the threaded portion of the stem and the mandrel and retaining the plug in assembled condition.

* * * * *